US012508152B2

(12) United States Patent

Lee et al.

(10) Patent No.: US 12,508,152 B2

(45) Date of Patent: Dec. 30, 2025

(54) OSTOMY POUCH

(71) Applicant: CONVATEC LIMITED, Flintshire (GB)

(72) Inventors: Bryony Lee, Flintshire (GB); Neal Carty, Chicago, IL (US); Monica Hill, Painsville, OH (US)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 18/991,956

(22) Filed: Dec. 23, 2024

(65) Prior Publication Data

US 2025/0127649 A1 Apr. 24, 2025

Related U.S. Application Data

(63) Continuation of application No. PCT/GB2023/052191, filed on Aug. 22, 2023.

(Continued)

(30) Foreign Application Priority Data

Oct. 18, 2022 (GB) ...................................... 2215377

(51) Int. Cl.

*A61F 5/445* (2006.01)
*A61F 5/44* (2006.01)
*A61L 28/00* (2006.01)

(52) U.S. Cl.

CPC .............. *A61F 5/445* (2013.01); *A61L 28/00* (2013.01)

(58) Field of Classification Search

CPC ......... A61F 5/445; A61F 5/4404; A61L 28/00
See application file for complete search history.

(56) References Cited

U.S. PATENT DOCUMENTS 5,455,091 A * 10/1995 Oreglia ................. B32B 27/304 428/36.1
5,837,352 A * 11/1998 English ................... B32B 5/022 604/358

(Continued)

FOREIGN PATENT DOCUMENTS

DE 10149975 A1 11/2002
GB 2310631 A 9/1997

(Continued)

OTHER PUBLICATIONS

International Preliminary Report on Patentability and Annexes from PCT/GB2023/05219; Completed Oct. 31, 2024; 16 pages.

(Continued)

*Primary Examiner* — Guy K Townsend
(74) *Attorney, Agent, or Firm* — TAFT STETTINIUS HOLLISTER LLP; Ryan O. White; Derek B. Lavender

(57) ABSTRACT

An ostomy pouch having a cavity for storing stomal output. The cavity is defined by a rear wall and a front wall joined at their peripheries and formed of flexible sheet material. The ostomy pouch further comprises a sheet of woven comfort material covering the outside surface of the front wall. The sheet of comfort material has an outside surface and an opposite inside surface, and the outside surface of the sheet of comfort material forms at least part of the outside surface of the pouch. The inside surface of the sheet of comfort material is laminated across its entire surface to a continuous layer of film material. At least part of the continuous layer of film material is adjacent, facing and unbonded to the outside surface of the front wall.

11 Claims, 7 Drawing Sheets

Related U.S. Application Data

(60) Provisional application No. 63/403,134, filed on Sep. 1, 2022.

(56) References Cited

U.S. PATENT DOCUMENTS

| | | | | |
|---|---|---|---|---|
| 2008/0294129 | A1* | 11/2008 | Giori | A61L 28/0057<br>428/35.2 |
| 2011/0028923 | A1* | 2/2011 | Murray | A61F 5/4405<br>604/332 |
| 2018/0333290 | A1* | 11/2018 | Jones | A61F 5/443 |
| 2021/0100677 | A1* | 4/2021 | Hoggarth | A61F 5/4405 |
| 2021/0100678 | A1* | 4/2021 | Hoggarth | A61F 5/4404 |
| 2021/0100679 | A1* | 4/2021 | Hoggarth | A61F 5/4404 |
| 2021/0100680 | A1* | 4/2021 | Hoggarth | A61F 5/4407 |
| 2021/0369484 | A1* | 12/2021 | Holden | A61F 5/445 |
| 2021/0369485 | A1* | 12/2021 | Evans | A61F 5/445 |
| 2021/0369486 | A1* | 12/2021 | Holden | A61F 5/441 |
| 2021/0369491 | A1* | 12/2021 | Holden | A61F 5/4404 |
| 2021/0369493 | A1* | 12/2021 | Young | A61F 5/4404 |
| 2021/0369494 | A1* | 12/2021 | Holden | A61F 5/448 |
| 2024/0082046 | A1* | 3/2024 | Holden | A61F 5/445 |

FOREIGN PATENT DOCUMENTS

| | | | | |
|---|---|---|---|---|
| WO | WO-2021064409 A1 | * | 4/2021 | A61F 5/4404 |
| WO | 2021245394 A1 | | 12/2021 | |

OTHER PUBLICATIONS

International Search Report and Written Opinion of ISA for PCT/GB2023/05219; mailed Jan. 31, 2024; 16 pages.

* cited by examiner

OSTOMY POUCH

CROSS REFERENCE TO RELATED DISCLOSURES

This disclosure is a continuation of International Application No. PCT/GB2023/052191 filed on Aug. 22, 2023 and claims the benefit of U.S. Provisional Application No. 63/403,134 filed Sep. 1, 2022 and foreign priority GB2215377.9 filed Oct. 18, 2022, the contents of which being incorporated herein by reference in entirety.

TECHNICAL FIELD OF THE INVENTION

The present invention relates to an ostomy pouch for managing effluent from a stoma.

BACKGROUND TO THE INVENTION

There are many forms of ostomy pouch, for example, open and closed, one-piece or two-piece. Pouches may have various shapes and various components. Typically they comprise a cavity formed of a (normally plastic) film, frequently formed by two layers, front and rear, welded together at their periphery, with the rear layer of film (closest to the ostomate's body in use) including an aperture through which effluent can enter the pouch.

For the comfort of the ostomate, a "comfort layer" can be provided, overlying the rear film layer, and normally the front film layer too. The comfort layer is made of a material that is more comfortable against the skin than the film. Normally, the comfort layer is a non-woven material—non-woven materials are chosen for features such as cost and ease of assembly, for example because they can be easily attached to the film layers of the pouch by the same welding process that bonds the film layers to one another at their periphery.

More recently, however, as part of efforts to make ostomy pouches seem less "medical", and more attractive to users, woven materials have been introduced as the comfort material of the Salts® Confidence BE® product, with the product being described in advertising material as "stylish". A woven material is more likely to be mistaken by others noticing the pouch as an undergarment, rather than as a medical appliance.

Whilst this is considered desirable, the production of an ostomy pouch with a woven comfort layer is considered to be complex. The Salts® Confidence BE® product appears to include a complete layer of specially chosen film material adjacent the woven layer. Thus in one example, moving from the ostomate out, there is: a rear woven comfort layer; an opaque rear wall defining one side of a cavity; a clear front wall defining the other side of the cavity; an opaque intervening wall; and, a front woven comfort layer. The front comfort layer is provided in two parts, top and bottom separated by a split and overlapping in the region of the split, so that the comfort layer can be pulled apart at the split to inspect the contents through the clear wall. The intervening layer is similarly provided in two parts, bonded (only) to the periphery of the two parts of the comfort layer. In this example, the intervening wall appears to avoid fraying of the edges of the comfort layer; avoid visibility of the contents; or aid in the processability of the (somewhat stretchy) fabric that it is adhered to.

This additional wall has a number of drawbacks for the pouch including: increased complexity of construction, increased cost; increased bulk, and increased noise in use as there is yet another (separate) layer which can rustle making the pouch less discreet.

Other prior art documents have also proposed use of woven materials as one option in comfort layers, for example, US2005/0273064 discloses a pouch which effectively integrates the walls of the pouch which form the cavity with the comfort layer. Thus a laminate is proposed including a fabric layer which can be a knit fabric, a woven fabric or a non-woven fabric, with the fabric layer adhered to a film layer by a layer of adhesive that substantially continuously bonds the fabric layer to the film layer. This arrangement, whilst requiring fewer layers than that of the Salts Confidence BE product suffers other disadvantages, for example, a typical comfort layer includes regions not adhered to the film layers that make up the cavity, such that the comfort layer can be pulled aside and the interior inspected, but this would not be possible with the pouch of US2005/0273064 on account of the comfort layer being substantially continuously bonded to the wall of the pouch.

WO2021/064409 also makes reference to a comfort layer comprising at least one fabric layer and at least one film layer, with the film layer optionally laminated to the at least one fabric layer over the entire area of the at least one fabric layer. No explanation is provided as to which side of the fabric layer should be provided with the film layer, nor any details of the lamination. In looking to work this aspect of the invention, those skilled in the art could be expected to use an intervening adhesive layer between the film and the fabric, just as in the laminate of US2005/0273064.

Against that background, PCT/GB2021/051340 proposed an ostomy pouch comprising a cavity for storing stomal output; the cavity defined by a rear wall and a front wall joined at their peripheries and formed of flexible sheet material as is typical. In this ostomy pouch, a sheet of woven comfort material covers the outside surface of the front wall and has a web of EVA hot-melt adhesive on the inside surface of the comfort material. Except at the periphery where the comfort material is bonded to the front wall, at least part of the web of EVA hot-melt adhesive is adjacent, facing and unbonded to the outside surface of the front wall.

In PCT/GB2021/051340 the web of hot melt adhesive comprises a mass and a plurality of voids in the mass which is considered to be advantageous over a "full film" in terms of requiring reduced material compared to a full film, as well as avoiding the rustling associated with films.

However, a disadvantage has been identified with using a web of EVA hot melt adhesive as disclosed in PCT/GB2021/051340, in that when the EVA-coated comfort material is attached at the periphery (P) of the pouch to the walls of the cavity (by plastic-welding) the hot melt adhesive leaks through the comfort material as shown in FIG. 9 causing darkened spots (S) which make the edge of the pouch unattractive.

It is an object of embodiments of the present invention to at least partially overcome or alleviate the above problems.

SUMMARY OF THE INVENTION

In this specification, the term "stomal output" refers to any gases or fluids or solids produced by an ostomate that may be secreted from the stoma or that exit the stoma. The stomal output may comprise stomal gas, stomal liquid and stomal solids.

In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the ostomy pouch disclosed herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

In this specification, the ostomy pouches disclosed herein may, for example, be used for managing a stoma created by an esophagostomy, a gastrostomy, a cholecystectomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy pouches disclosed herein may be used with additional devices including, but not limited to, a shunt, a catheter, a plug or a fecal management system.

Beneficially, the ostomy pouches of the present disclosure may permit an ostomate to increase the period of use of each ostomy pouch compared to prior art pouches. This may be achieved, for example, by providing an increased cavity volume for the ostomy pouch while maintaining ostomate discretion and comfort. Additionally or alternatively, this may also be achieved by providing means for draining the cavity of stomal output reliably and hygienically so as to increase an ostomate's confidence in reusing the ostomy pouch compared to some prior art pouches. Since the ostomate may be inclined to use each ostomy pouch of the present disclosure for longer, the total number of ostomy pouches used by the ostomate in a given time period may be reduced. This may produce an environmental benefit in reducing the amount of environmental waste produced.

In this specification locations and orientations of features may be described with reference to the ostomy pouch being "in use", "orientated as it would be in use" or similar. Such terms refer to the intended orientation of the ostomy pouch when it is adhered to a body of an ostomate with the ostomate in a standing position, irrespective of whether the ostomy pouch is currently performing such a use or the actual position of the ostomate. The terms "upper" and "lower" and related terms refer to the relative position of a part or portion of the ostomy pouch when orientated as it would be in use. For example, a section of the ostomy pouch may be referred to as an "upper" section of the ostomy pouch. In such an example, said section will be intended to be the uppermost section (in the vertical direction) of the ostomy pouch when attached to the body of a standing ostomate. However the reader skilled in the art will appreciate that before attachment to the ostomate said section may not always be the uppermost section and in addition when attached the section may not always be the uppermost section if the ostomate adopts a non-standing position, for example lying down.

The terms "left-hand" and "right-hand" and related terms refer to the ostomy pouch when viewed from the rear (for example, as shown in FIG. 1). Thus, as an illustrative example, a "left-hand" edge of the ostomy pouch will be towards a left-hand side of the ostomate in the situation where the ostomy pouch is attached to the front torso of the ostomate.

The terms "concave" and "convex" and related terms refer to shaping of features of the ostomy pouch when viewed from an exterior of the ostomy pouch. Thus, as an illustrative example, an ostomy wafer of circular shape would be considered to have a convexly shaped peripheral edge.

In this specification the terms "front" and "rear" refer to the relative position of a part or portion of the ostomy pouch with reference to the body of an ostomate when the ostomy pouch is attached to the body. "Rear" refers to a position relatively closer to the body of the ostomate than a comparative position that is "front". "Front" refers to a position relatively further away from the body of the ostomate than a comparative position that is "rear".

In this specification the term "smoothly blends" and related terms refers to the smooth merging of two edges, lines or contours without abrupt changes in contour.

In this specification the term "peripheral region" refers to a portion situated on or towards an edge of the item being referred to.

The term "turned up" used herein may include folding or rolling of the components.

Ostomy pouches are commonly attached to the body by means of an ostomy wafer which includes an adhesive layer or layers. The ostomy wafer typically has an opening for the stoma sometimes referred to as a starter hole which may be cut to a required size by a user before attachment. The ostomy wafer typically comprises an adhesive layer on a body-facing side for adhering the ostomy wafer to the body of the ostomate. Typically, a release liner covers a body-facing side of the ostomy wafer that is removed by the user prior to fitting to the skin. In this specification, the term "ostomy wafer" may be used interchangeably with the terms "adapter," "wafer," "baseplate", or "layered adhesive wafer." In this specification, the term "ostomy wafer" includes ostomy wafers for a "two-piece pouch" and for a "one-piece pouch".

In this specification a "two-piece pouch" refers to a pouch where the ostomy wafer forms part of a separate body fitment component that is attached by a releasable coupling to the remainder of a pouch. A two-piece pouch permits the body fitment component to be separated from the pouch without damage, so that at least one of the parts continues to be functionally usable. For example, the body fitment component may remain in place on the body of the ostomate.

In this specification a "one-piece pouch" refers to a pouch where the ostomy wafer is permanently attached to the pouch, to the extent that the ostomy wafer cannot easily be separated without risk of damaging the pouch. A one-piece pouch is intended to be used as an integral unit.

Ostomy pouches are commonly configured as closed pouches or open pouches. In this specification a "closed pouch" refers to an pouch where it is not intended that stomal output is drained from the cavity. Thus, a closed pouch may typically be configured as a one-use, disposable and non-reusable pouch. In this specification an "open pouch" refers to an pouch where it is intended that stomal output is drained from the cavity. Thus, an open pouch may be configured as a reusable pouch, such that it can be reused and emptied multiple times whilst attached to the body, although this is not essential. In an open pouch the stomal output may be drained intermittently as instigated by an action of the ostomate or may be drained intermittently or continuously due to the cavity being fluidly connected to a drain, for example a night drain line.

The present invention provides an ostomy pouch. In particular, the invention provides an ostomy pouch having a sheet of comfort material with a layer of film material laminated across its inside surface. At least part of the inside surface may be adjacent, facing and unbonded to a cavity for storing stomal output. The cavity may be defined by a rear wall and a front wall, which may be joined at their peripheries and may be formed of flexible sheet material. The comfort material may be woven. The sheet of comfort material may cover the outside surface of the front wall. The sheet of comfort material may have an outside surface and an opposite inside surface. The outside surface of the sheet of comfort material may form at least part of the outside surface of the pouch. The inside surface of the sheet of comfort material may be laminated across its entire surface to the layer of film material. The layer of film material may be a continuous layer of film material. At least part of the continuous layer of film material may be adjacent, facing and unbonded to the outside surface of the front wall.

According to a broad aspect of the present invention, there is provided an ostomy pouch comprising a cavity for storing stomal output; the cavity defined by a rear wall and a front wall joined at their peripheries and formed of flexible sheet material; the ostomy pouch further comprising a sheet of comfort material covering the outside surface of the front wall; the sheet of comfort material having an outside surface and an opposite inside surface, wherein the outside surface of the sheet of comfort material forms at least part of the outside surface of the pouch, and the inside surface of the sheet of comfort material is laminated across its entire surface to a continuous layer of film material; at least part of the continuous layer of film material being adjacent, facing and unbonded to the outside surface of the front wall. The comfort material may be a woven material. The continuous layer of film material may be laminated to the comfort material with no intervening adhesive.

According to a first aspect of the present invention, there is provided an ostomy pouch comprising a cavity for storing stomal output; the cavity defined by a rear wall and a front wall joined at their peripheries and formed of flexible sheet material; the ostomy pouch further comprising a sheet of woven comfort material covering the outside surface of the front wall; the sheet of comfort material having an outside surface and an opposite inside surface, wherein the outside surface of the sheet of comfort material forms at least part of the outside surface of the pouch, and the inside surface of the sheet of comfort material is laminated across its entire surface to a continuous layer of film material, with no intervening adhesive; at least part of the continuous layer of film material being adjacent, facing and unbonded to the outside surface of the front wall.

A continuous layer of film material may be understood to mean an uninterrupted layer, it may equally be understood as a "solid" layer having no voids, in contrast to that of PCT/GB2021/051340.

Such layers of film material do not have the same propensity to leak through a woven material when the comfort material is welded to the walls of the cavity-because forming a web, mesh, net or the like, typically requires a spray coating technique (either spraying onto the comfort material, or spraying to form a layer, that is formed into a roll and laminated to the comfort material (as disclosed in PCT/GB2021/051340)); as such, to be spray-coated, the inventors understand that the EVA hot melt adhesive must necessarily have a relatively low viscosity, or other characteristics which lead to the problematic leaking through the comfort material. Without being bound by the theory, the inventors believe that a material with a higher viscosity will be less likely to flow through the comfort material and can be easily produced as a continuous film; as such, those skilled in the art can, in light of this disclosure, easily select continuous films with appropriate characteristics to avoid this issue.

Obviously, as compared to the Salts® Confidence BE® product the ostomy pouch of the first aspect of the invention has advantages such as the lack of a separate intervening layer, hence less rustling. Moreover, as the film layer is laminated to the woven comfort material, with no intervening adhesive layer, the process of attaching the comfort layer to the cavity is simplified, because the already-laminated woven layer can be attached directly to the films forming the cavity, so fewer rolls of material need to be joined in the manufacturing process.

As compared to US2005/0273064, of course, the advantages are much the same as they are in PCT/GB2021/051340.

The continuous layer of film material may have an even thickness (i.e. a substantially even thickness) across the entire surface of the sheet of woven comfort material. The deviation in thickness across the entire surface of the film material may be less than 10 microns, preferably less than 5 microns, more preferably less than 3 microns, such as less than 2 microns.

The continuous layer of film material may have a thickness (i.e. an average thickness) of less than 60 microns (preferably less than 40 microns, more preferably less than 30 microns) across the entire surface of the sheet of woven comfort material. The continuous layer of film material may have a thickness of at least than 10 microns (preferably more than 15 microns, more preferably more than 20 microns) across the entire surface of the sheet of woven comfort material. For example, the continuous layer of film material may have a thickness of between 20 and 30 microns, e.g. 23 to 27 microns, such as about 23 microns across the entire surface of the sheet of woven comfort material.

The continuous layer of film material may have an area density of at least 0.5, 1, 5, 10, 15, 16 or 20 $g/m^2$, and/or no more than 500, 100, 50, 40, 35, 30 or 25 $g/m^2$ preferably 10-50 $g/m^2$, 16-35 $g/m^2$, 18-30 $g/m^2$, or 20-25 $g/m^2$, for example 23 $g/m^2$.

Accordingly in one preferred embodiment there is provided an ostomy pouch comprising a cavity for storing stomal output; the cavity defined by a rear wall and a front wall joined at their peripheries and formed of flexible sheet material; the ostomy pouch further comprising a sheet of woven comfort material covering the outside surface of the front wall; the sheet of comfort material having an outside surface and an opposite inside surface, wherein the outside surface of the sheet of comfort material forms at least part of the outside surface of the pouch, and the inside surface of the sheet of comfort material is laminated across its entire surface to a continuous layer of film material, with no intervening adhesive; at least part of the continuous layer of film material being adjacent, facing and unbonded to the outside surface of the front wall; wherein the continuous layer of film material has an area density of 18-30 $g/m^2$.

The continuous layer of film material is formed of a material which bonds to the material of the comfort layer without the need for an intervening adhesive. As such, the continuous layer of film material may be a continuous layer of hot-melt adhesive material.

The continuous layer of film material may be formed of the same material as the front wall and the rear wall. This improves attachment of the comfort material to the cavity, because the two materials will typically melt at the same temperature in a plastic-welding step and bond well to one another.

The continuous layer of film material and the front and rear walls may be formed of polymers with the same chemical structure. The continuous layer of film material and the front and rear walls may be formed of polymers with the same molecular weight $M_n$. The continuous layer of film material and the front and rear walls may be formed of polymers with the same melting point, $M_p$. The continuous layer of film material and the front and rear walls may be formed of polymers obtained from the same source, with the same designation. Using polymers obtained from the same source, and having the same designation should ensure that other characteristics defining the similarity (e.g. structure, $M_n$, $M_p$) can be relied upon to be the same, without the need for measurement.

The continuous layer of film material is preferably formed of EVA. The continuous layer of film material may alternatively be formed of another plastics material, for example polyethylene, provided the film is selected to have suitable properties in terms of being able to bond to the comfort material without an intervening adhesive layer and without leaking through.

The pouch may have a front and a rear. The sheet of woven comfort material may form at least part of the front surface of the pouch. The front and rear surfaces of the pouch may be both formed by sheets of woven comfort material. As such, the ostomy pouch may further comprise a sheet of woven comfort material covering the outside surface of the rear wall; the sheet of comfort material having an outside surface and an opposite inside surface, wherein the outside surface of the sheet of comfort material forms at least part of the outside surface of the pouch, and the inside surface of the sheet of comfort material is laminated across its entire surface to a continuous layer of film material; at least part of the continuous layer of film material being adjacent, facing and unbonded to the outside surface of the rear wall.

Such an embodiment of the present invention therefore provides a pouch covered on both sides (front and rear) in woven comfort material that provides enhanced comfort for the user and which has a continuous layer of film material laminated to the sheet of comfort material so that the pouch can be easily manufactured without additional welding steps or the introduction of intermediate layers and does not suffer from adhesive leaking through the comfort layer. Effectively, the laminated sheets of comfort material can be bonded to the remainder of the pouch, for example a front wall defining one side of a cavity and a rear wall defining the other side of a cavity, in just the same way as a non-woven material would be bonded—typically a single step welding process whereby the peripheries of all the layers are bonded to each other.

The woven comfort material may comprise a natural material, for example cotton or wool and/or a synthetic material, for example any one or more of polyester, nylon, viscose, polyethylene, polypropylene, or the like. The woven material may have an area density of 20 to 200 g/m$^2$, preferably 40-80 g/m$^2$, for example 58 g/m$^2$. The woven material may have a tensile strength of 200 to 400 N, preferably 250 to 350 N, for example 300N in the warp and 280 N in the weft. The woven material may have a tear strength of 5 to 50 N, preferably 10-30 N, for example 18 N. The woven material may have a colour fastness to any one or more of rubbing, perspiration or washing (40°) of 4 to 5. The woven material may have an abrasion of >50,000. The woven material may have a water resistant finish. For example, it may comprise woven polyester with a water repellent finish. The water repellent finish may be fluorocarbon based. The water repellent finish may be dyed heat set or boil off heat set.

The woven comfort layer may have a thickness of 50 to 1000 micrometres, preferably 60 to 500 micrometres, more preferably 75 to 300 micrometres.

The rear wall and front wall may be substantially the same shape. The rear wall and front wall may be formed of plastics film. The rear wall and/or front wall may be opaque. The rear wall and/or front wall may be transparent. In particular at least part of the front wall may be transparent. The rear wall and/or front wall may be formed for example of any one of polyurethane, polyethylene (PE), polyvinylidene chloride (PVDC), or ethylene-vinyl acetate (EVA). The rear wall and/or front wall may each have a thickness of 50 to 150 μm. The rear wall and/or front wall may each have a thickness of 75 to 100 μm. The rear wall and front wall may have corresponding inside and outside surfaces. The inside surfaces of the rear and front walls may form the interior of the cavity. The outside surfaces of the rear and front walls may form the exterior of the cavity. The sheet of woven comfort material may be substantially the same shape as the front wall. A/the sheet of comfort material may be bonded to the outside surface of a wall of the cavity at the periphery, but unbonded to the wall other than at the periphery.

The sheet of woven comfort material covering the front of the pouch may comprise one or more parts. The sheet of woven comfort material covering the front of the pouch may comprise an upper part and a lower part. The upper part and lower part when taken together may be the same shape as the front wall. The upper part may extend from a top edge of the pouch to a point 20-50% down its length from the top. The lower part may extend from a bottom edge of the pouch to a point 15-50% down its length from the top. An overlap region may be provided where the upper part and lower part overlap. The upper part may extend over the lower part (or vice versa) to form the overlap in the overlap region. The upper part and the lower part may be separable from each other in the overlap region. The overlap region may extend horizontally when the ostomy pouch is in use. Thus, especially when the front wall is formed of a transparent film, the present invention provides a device that can permit convenient viewing of the stoma and/or the contents of the pouch if required.

The pouch may comprise a drain. The drain may be disposed at the bottom of the pouch in use. The drain may be formed from the front and rear walls of the pouch. The drain may be rectangular. The drain may be foldable. The drain may be foldable along its length. The drain may be movable between a folded and unfolded configuration. The drain may be in a closed state in its folded configuration. The drain may be in an open state in its unfolded configuration. When open, the drain may permit stomal output to leave the cavity of the pouch. When closed, the drain may prevent stomal output leaving the cavity of the pouch.

The drain may be provided with one or more pursing strips. The or each pursing Strip may span the width of the drain. The or each pursing strip may extend the same distance along the length of the drain. The or each pursing strip may provide localised rigidity to the drain. The or each pursing strip may be formed from polystyrene. The or each pursing strip may define the locations and orientations of one or more folds of the drain. The or each pursing strip may comprise a strip of flexible material attached drain. The strip may have a higher rigidity than the material of the drain. The or each pursing strip may have some resilience once attached to the drain. Therefore, the pursing strips can be squeezed laterally to arch the pursing strip and thereby assist in opening the drain.

A pursing strip may be provided on the rear wall. The pursing strip may be provided adjacent a bottom end of the drain. The pursing strip may be provided on the outside surface of the rear wall. A pursing strip may be provided on the front wall. The front wall pursing strip may be provided on the outside surface of the front wall. The front wall pursing strip may be provided above the rear wall pursing strip. The front wall pursing strip may be provided midway between a top end and the bottom end of the drain. A longitudinal gap may be provided between an upper edge of the rear wall pursing strip and a lower edge of the front wall pursing strip. The longitudinal gap may define the location of a first fold of the drain.

A fastening element may be disposed on an outside surface of the rear wall. The rear fastening element may be disposed above the front pursing strip. A longitudinal gap may be provided between an upper edge of the front wall pursing strip and a lower edge of the second fastening element. The longitudinal gap may define the location of a fold of the drain. The rear fastening element may be disposed adjacent the top end of the drain.

A closure mechanism for the drain of the ostomy pouch may be attached to a sheet of comfort material covering the front of the pouch. The closure mechanism may be attached to the outside surface of the comfort material. The closure mechanism may be a closure flap. The closure flap may be welded to the woven comfort material. The weld may be along a top edge of the closure flap. The closure flap may have an outside surface and an inside surface. The inside surface of the closure flap may be adjacent the outside surface of the comfort material. The closure mechanism may comprise a front fastening element. The front fastening element may co-operate to fasten with the rear fastening element. Fastening of the fastening elements may close the drain.

The closure flap may comprise a woven comfort material (optionally comprising the continuous layer of film material). This is desirable as forming the closure flap of the same material as the comfort material makes it more subtle/discreet.

The front fastening element may be disposed above the rear fastening element. The front fastening element may be disposed adjacent a bottom edge of the comfort material. A longitudinal gap may be provided between an upper edge of the rear fastening element and a lower edge of the front fastening element. The longitudinal gap may define the location of a fold of the drain. The rear fastening element may be disposed adjacent the top end of the drain.

The drain may be closed by repeatedly folding the drain upwards about the fold lines defined by the front and rear pursing strips and front and rear fastening elements. The folded drain may be retained between the woven comfort material and closure flap. The sides of the closure flap may not extend beyond the edges of the comfort material. The closure flap may comprise a tab. The tab may extend beyond the bottom edge of the comfort material. The front and rear fastening elements may be the same size. The front and rear fastening elements may not span the width of the drain.

Therefore, the drain can be conveniently closed against the comfort material and secured in place with the closure flap. It is therefore not necessary to fold or secure the drain beneath the comfort material, making the pouch easier to use. The provision of a tab makes unfolding of the drain easier as the closure flap can be lifted allowing access to undo the fastening elements, as does the inclusion of fastening elements that do not span the entire drain width.

According to a second aspect of the invention, there is provided a method of forming a comfort layer laminate for bonding to a cavity of an ostomy pouch; the method comprising laminating a continuous layer of film material directly to a sheet of comfort material, with no intervening adhesive layer.

Preferably the continuous layer of film material is laminated to the sheet of comfort material under conditions of elevated (w.r.t ambient) temperature and pressure, for example by calendaring.

Of course, the comfort layer and the film material may have any of the features outlined above, such as the materials outlined, and/or the maximum thickness, which makes the layer of film material suitable as a backing for a comfort layer, which should be easily conformable, but unsuitable for forming a wall of a cavity.

Thus, for example, in one embodiment the layer of comfort material is woven. So there is provided a method of forming a comfort layer laminate for bonding to a cavity of an ostomy pouch; the method comprising laminating a continuous layer of film material directly to a sheet of woven comfort material, with no intervening adhesive layer.

Naturally, the method should form a material in which the layer of comfort material remains continuous, i.e. no steps in the method should introduce voids or apertures. As such in one embodiment there is provided a method of forming a comfort layer laminate for bonding to a cavity of an ostomy pouch; the method comprising laminating a continuous layer of film material directly to a sheet of comfort material, with no intervening adhesive layer to form a sheet of woven comfort material having an outside surface and an opposite inside surface, wherein the inside surface of the sheet of comfort material is laminated across its entire surface to a continuous layer of film material, with no intervening adhesive; the continuous layer of film material being an uninterrupted, "solid" layer having no voids.

According to a third aspect of the present invention, there is provided a method of forming an ostomy pouch, the method comprising providing a sheet of comfort material having a continuous layer of film material laminated across the entirety of a first surface, and bonding only part of the first surface of the sheet of comfort material to the outside surface of a wall of a cavity of the ostomy pouch, whereby at least part of the continuous layer of film material is adjacent, facing and unbonded to the outside surface of the front wall.

The sheet of comfort material having a continuous layer of film material laminated across the entirety of a first surface, is preferably formed in accordance with the second aspect of the invention.

As such, a preferred method of forming an ostomy pouch comprises first forming a comfort layer laminate for application to a cavity of an ostomy pouch; the method comprising laminating a continuous layer of film material directly to a sheet of comfort material, with no intervening adhesive layer, to provide a sheet of comfort material having a continuous layer of film material laminated across the entirety of a first surface; and then forming an ostomy pouch, by bonding only part of the first surface of the sheet of comfort material to the outside surface of a wall of a cavity of the ostomy pouch whereby at least part of the continuous layer of film material is adjacent, facing and unbonded to the outside surface of the front wall.

The step laminating a continuous layer of film material directly to a sheet of comfort material, may be conducted separately from the step of bonding the inside surface of the sheet of woven comfort material to a wall of the pouch. For example, it may be conducted temporally separately, e.g. a least 5 minutes, 10 minutes, 1 hour, 12 hours, or 24 hours before bonding the inside surface of the sheet of comfort material to the wall. Alternatively/additionally, the step of laminating a continuous layer of film material directly to a sheet of comfort material may be conducted physically separately from the step of bonding the inside surface of the sheet of woven comfort material to a wall of the pouch. For example it may be conducted in a separate room, separate building or separate city, county or state.

Accordingly, in one embodiment, there is provided a method of forming an ostomy pouch comprising first forming a comfort layer laminate for application to a cavity of an ostomy pouch; the method comprising laminating a continuous layer of film material directly to a sheet of comfort material, with no intervening adhesive layer, to provide a sheet of comfort material having a continuous layer of film material laminated across the entirety of a first surface; and then forming an ostomy pouch, by bonding only part of the first surface of the sheet of comfort material to the outside surface of a wall of a cavity of the ostomy pouch whereby at least part of the continuous layer of film material is adjacent, facing and unbonded to the outside surface of the front wall; wherein the step laminating a continuous layer of film material directly to a sheet of comfort material, is conducted temporally separately from the step of bonding the inside surface of the sheet of woven comfort material to a wall of the pouch, at least 12 hours before bonding the inside surface of the sheet of comfort material to the wall.

Preferably the method comprises bonding the first surface of the sheet of comfort material to the periphery of the wall of the cavity of the ostomy pouch. preferably the method of bonding is welding.

Preferably the cavity is defined by a rear wall and a front wall joined at their peripheries and formed of flexible sheet material. The method may comprise providing a rear wall and a front wall formed of flexible sheet material and joining them at their peripheries. The method may include bonding the inside surface of the sheet of comfort material to one or more of the rear and/front wall of the ostomy pouch at the periphery thereof. The method may comprise simultaneously joining the front wall and the rear wall of the cavity, and bonding part of the first (inside) surface of the sheet of comfort material to at least one of the walls of the cavity.

The sheet of comfort material may comprise two or more parts and the method may include arranging a plurality of parts of a sheet of comfort material, and bonding the plurality of parts of a sheet of comfort material to the pouch. The bonding of the plurality of parts may be performed simultaneously. The bonding may be performed by welding. Thus, the present invention allows for complex arrangements of material to be applied to the pouch in a single manufacturing step, reducing the complexity and cost of production.

According to a fourth aspect of the invention there is provided an ostomy pouch formed by the method of the third aspect of the invention. Again, of course, the ostomy pouch may be an ostomy pouch according to the broad aspect or first aspect above, and may have any of the optional features set out above.

According to a fifth aspect of the invention, there is provided a method for collecting stomal output using an ostomy pouch according to any aspect described herein. The method may comprise attaching the ostomy pouch about a stoma of an ostomate. The ostomy pouch may be attached about the stoma through use of an ostomy wafer of the pouch where the pouch comprises a one-piece ostomy pouch. Alternatively, the method may comprise attaching an ostomy wafer of a body fitment component of a two-piece ostomy pouch about the stoma; and attaching a pouch to the body fitment component. The pouch may be attached to the body fitment component before or after the ostomy wafer has been attached about the stoma. Where the ostomy pouch comprises an open or drainable pouch, the method may comprise draining stomal output from the ostomy pouch.

Again, the fifth aspect of the invention may include any optional feature associated with any of the first to fourth aspects of the invention.

DETAILED DESCRIPTION OF THE INVENTION

In order that the invention may be more clearly understood one or more embodiments thereof will now be described, by way of example only, with reference to the accompanying drawings, of which:

Figure 6:
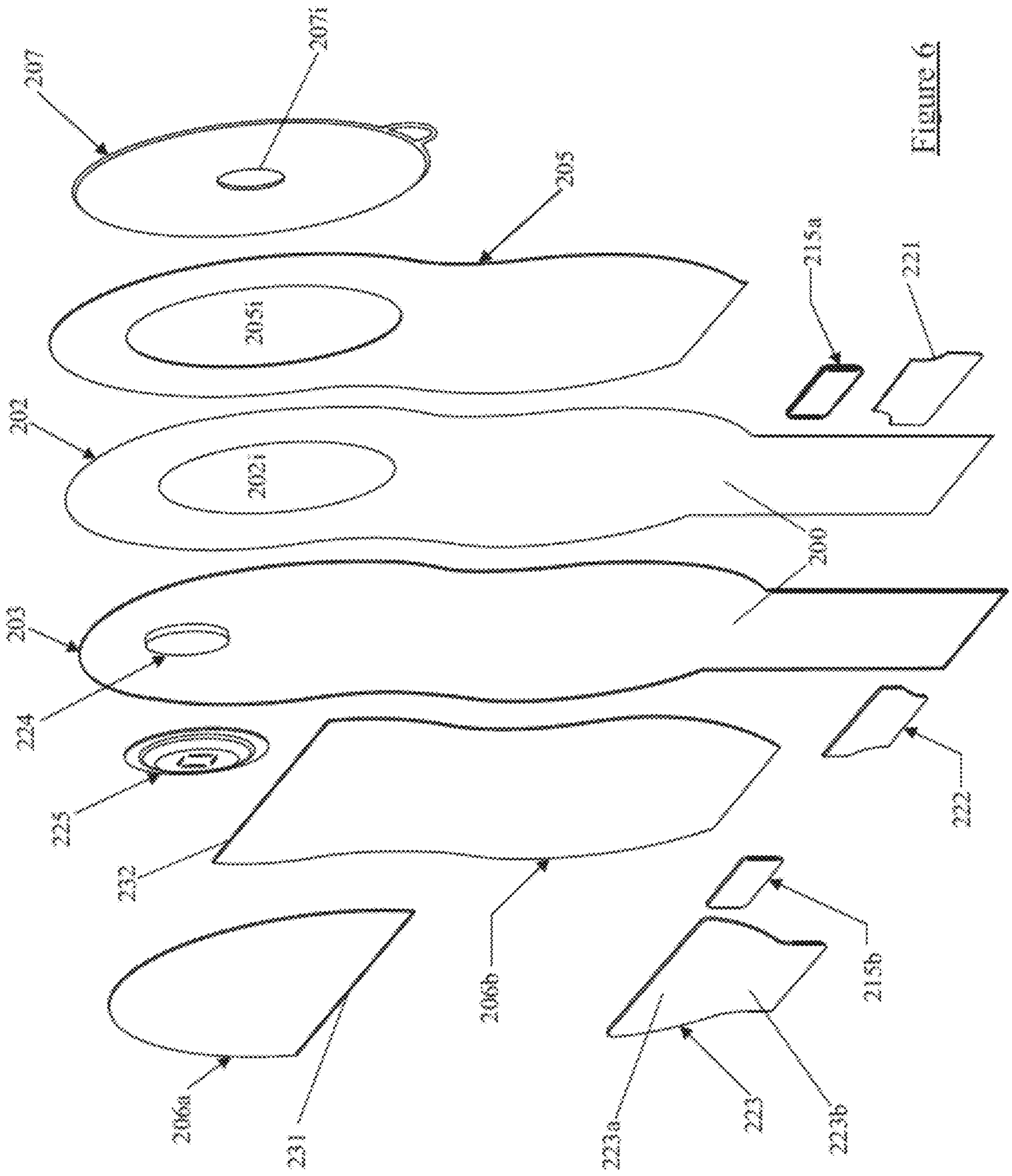
FIG. 6 is an exploded perspective view of the ostomy pouch of FIG. 4.
Figure 7:
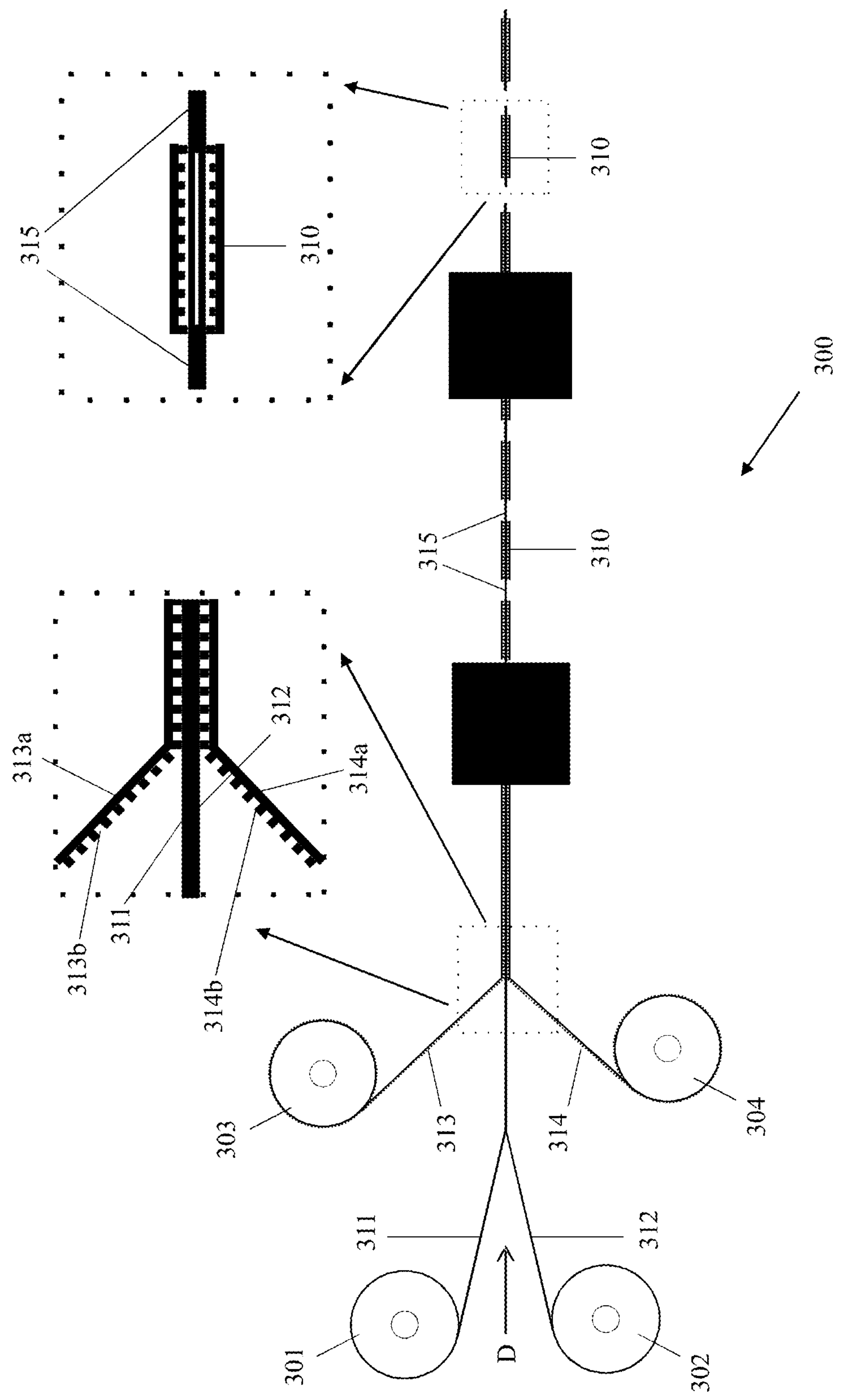
FIG. 7 is a side view of an apparatus for producing an ostomy pouch.
Figure 8:
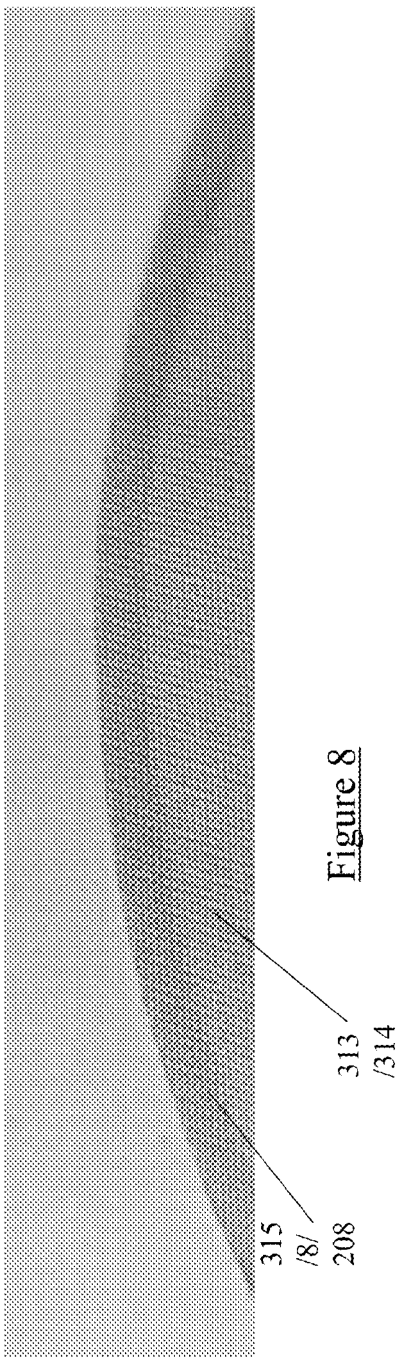
Figure 9:
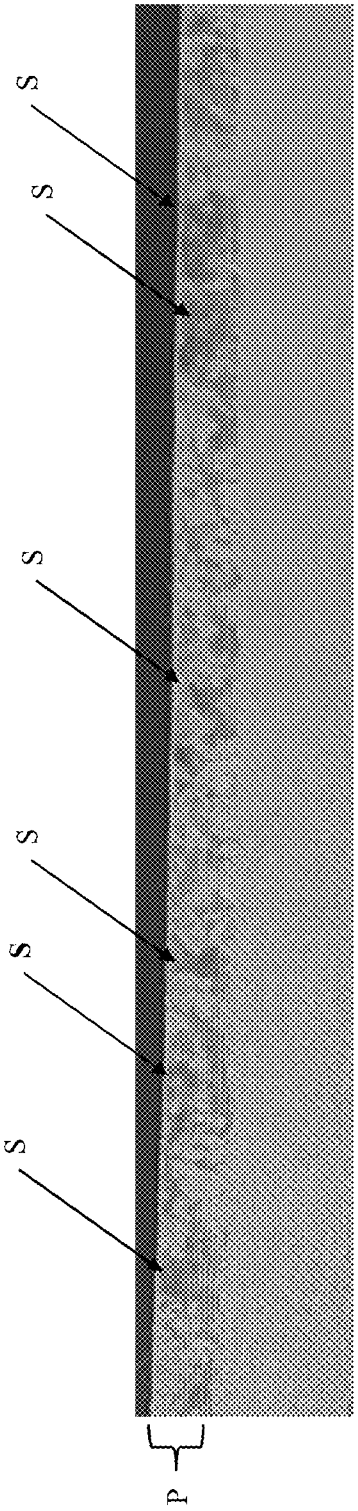

FIG. 8 is a partial view of an ostomy pouch according to any of the embodiments of FIGS. 1-8 showing the absence of leakage of the laminated film layer through the woven comfort material in the region where the comfort material is bonded to the cavity; and FIG. 9 is a partial view of a an ostomy pouch with layer of comfort material manufactured in accordance with a prior art method, showing the leakage of the hot melt adhesive through the woven comfort material in the region where the comfort material is bonded to the cavity.

Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

In this specification, the use of the singular includes the plural unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 mm" means "about 5 mm" and also "5 mm." Generally, the term "about" includes an amount that would be expected to be within experimental error. The term "about" includes values that are within 5% less to 5% greater of the value provided. For example, "about 30 mm" means "between 28.5 mm and 31.5 mm."

Figure 1:
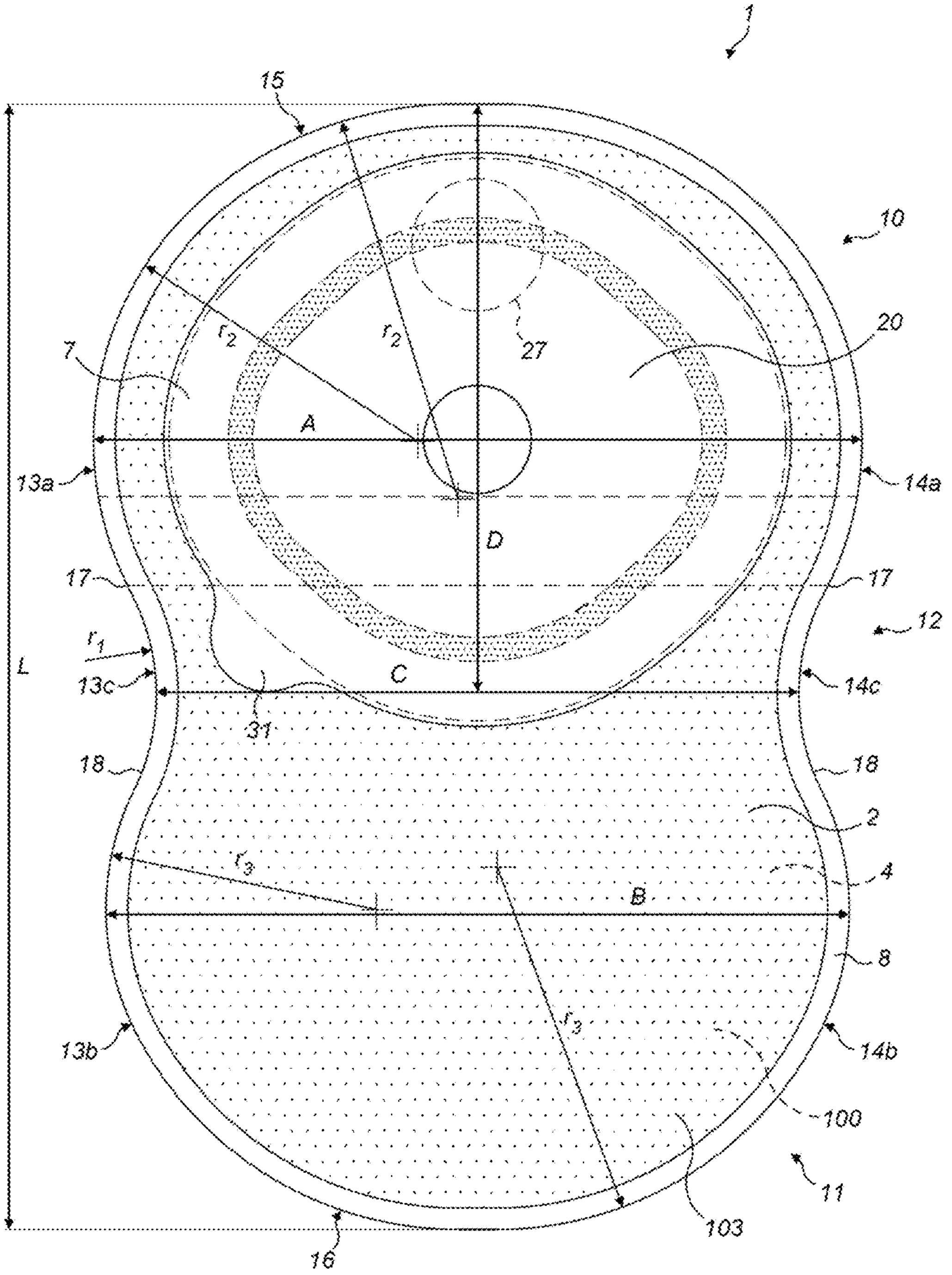
FIG. 1 is a rear view of an ostomy pouch.
Figure 2:
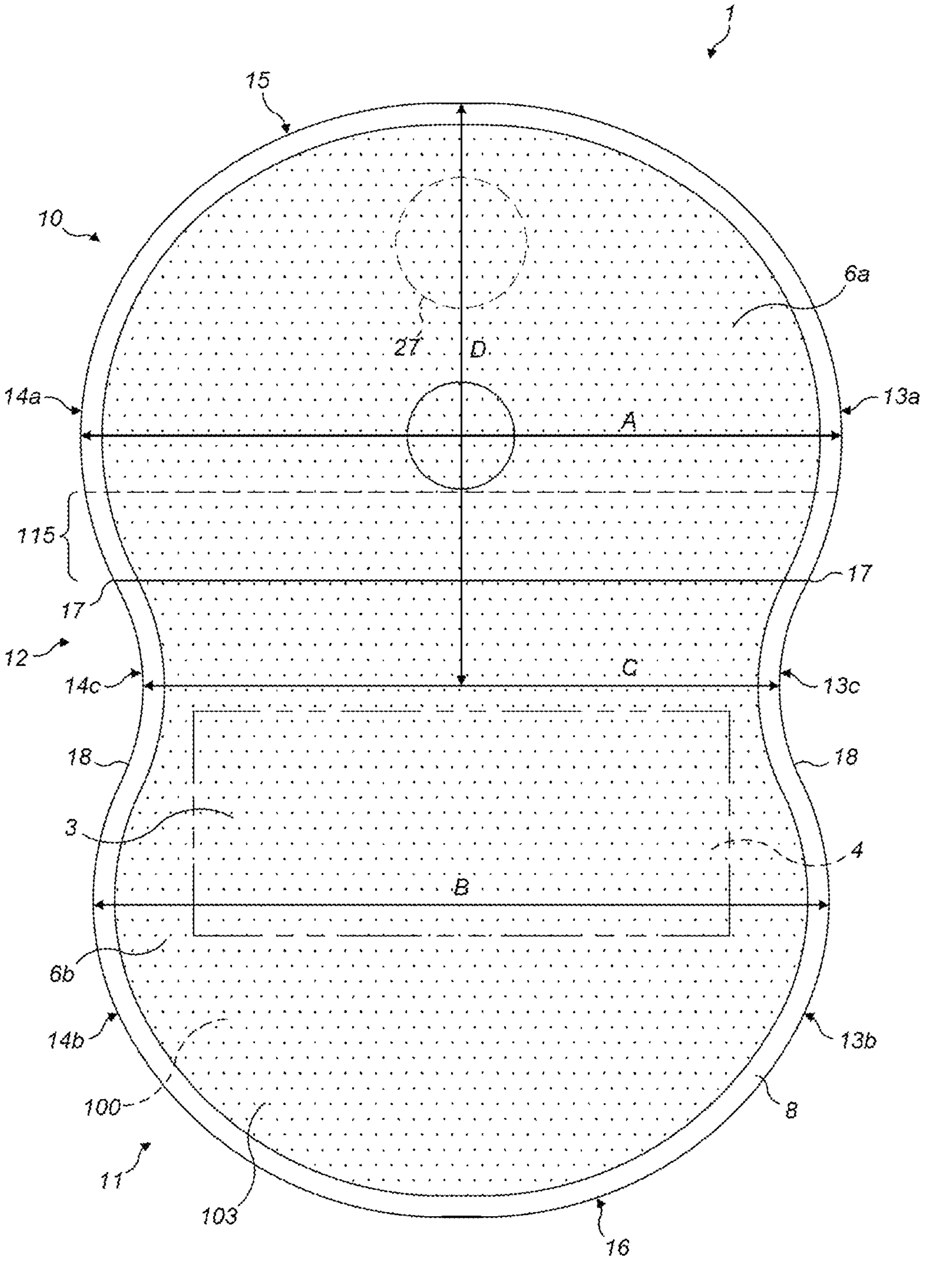
FIG. 2 is a front view of the ostomy pouch of FIG. 1.
Figure 3:
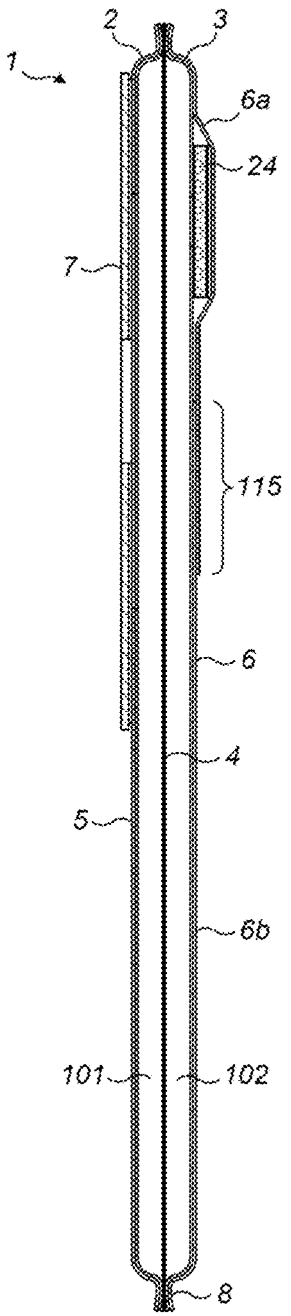
FIG. 3 is a cross-sectional side view of the ostomy pouch of FIG. 1.

Referring to FIGS. 1 to 3, an embodiment of the invention is shown in which an ostomy pouch 1 comprises a rear wall 2, a front wall 3, a separation wall 4, a rear comfort layer 5, a front comfort layer 6 and an ostomy wafer 7. In other embodiments within the ambit of the invention as claimed, one or more of the separation wall 4, the rear comfort layer 5 and the front comfort layer 6 may be omitted if desired.

In this embodiment, the ostomy pouch 1 is a one-piece pouch wherein the ostomy wafer 7 is permanently attached to the ostomy pouch 1 (in the sense that it cannot be easily removed and re-attached without damaging the pouch). However, other embodiments may be a two-piece pouch comprising a pouch component and body fitment component that together form the ostomy pouch. In some of these embodiments, the pouch comprises the rear wall 2, the front wall 3, the separation wall 4, the rear comfort layer 5 and the front comfort layer 6, and the body fitment component comprises the ostomy wafer 7.

The rear wall 2 and the front wall 3 define a cavity for containing a stomal output. In this embodiment, the rear wall 2 and the front wall 3 are both formed of flexible sheet material in the form of a plastics film and are joined together to define the cavity. An exemplary film is Ethylene-vinyl acetate (EVA). The film typically has a thickness of 75 to 100 μm but in some embodiments may have a thickness of 50 to 150 μm.

In this embodiment, the ostomy pouch 1 has an upper section 10, a lower section 11 and a waisted section 12 that is located between the upper section 10 and the lower section 11. The upper section 10 has a maximum width, A, the lower section 11 has a maximum width, B, and the waisted section, 12, has a minimum width, C. In this embodiment, the maximum width, A, of the upper section 10 is greater than the maximum width, B, of the lower section 11, which in turn is greater than the minimum width, C, of the waisted section 12.

In this embodiment, the ostomy pouch 1 has a left-hand 13 and right-hand 14 edge when viewed from the rear. The waisted section 12 has a left-hand edge 13*c* and a right-hand edge 14*c* that are both smoothly rounded and merge into the respective left-hand edges 13*a*, 13*b* and right-hand edges 14*a*, 14*b* of the upper section 10 and the lower section 11.

The shape and dimensions of the ostomy pouch 1 are not particularly limited so long as it remains discreet and comfortable to wear in use. Exemplary dimensions and other suitable shapes are set out in the prior art documents cited in the introduction, such as PCT/GB2021/051340, which is incorporated by reference.

In this embodiment, the left-hand edge 13*c* and the right-hand edge 14*c* of the waisted section 12 have concave curvature with a radius of curvature, r1.

In this embodiment, both the upper 10 and lower 11 sections are rounded and comprise continuously curved edges 15, 16 respectively. The curved edges 15, 16 extend from the upper and lower ends of left-hand edge 13*c* of the waisted section 12 to the corresponding upper and lower ends of the right-hand edge 14*c* of the waisted section 12. The edges 15, 16 are convexly curved with a radius of curvature of r2 and r3 respectively. In this embodiment, the r2 and r3 are constant along their respective edges 15, 16, however in alternative embodiments they may be variable.

In this embodiment, the upper section edge 15 incorporates the left-hand edge 13*a* and the right-hand edge 14*a* of the upper section 10 while the lower section edge 16 incorporates the corresponding left-hand 13*b* and right-hand edge 14*b* of the lower section.

In this embodiment, a junction between the upper section 10 and the waisted section 12 may be demarcated by a single point of inflection 17 between the edges 13*a*, 14*a* of the upper section 10 and the edges 13*c*, 14*c* of the waisted section 12. Similarly, a junction between the lower section 11 and the waisted section 12 may be demarcated by a single point of inflection 18 between the edges 13*b*, 14*b* of the lower section 11 and the edges 13*c*, 14*c* of the waisted section 12.

The rear wall 2 and front wall 3 are joined around their peripheral edges by use of welding. Welding is a preferred method of joining the rear wall 2 and the front wall 3 as it allows all the layers of the pouch 1 to be joined simultaneously, as described later.

In this embodiment, the rear wall 2 and the front wall 3 are joined together by a single continuous edge seal 8 that extends around a full perimeter of the rear wall 2 and the front wall 3 to create a fluid-tight seal.

The rear wall 2 is provided with a stomal inlet 20 for receiving the stomal output into the cavity. The stomal inlet 20 is an aperture that is cut out of the rear wall 2 in the upper section 10 of the ostomy pouch 1, in which the wafer 7 is provided, the wafer having a hole through which a stoma normally extends.

In this embodiment, the rear comfort layer 5 and front comfort layer 6 are substantially the same shape as the rear 2 and front 3 walls. The rear 5 and front 6 comfort layers form the outside of the ostomy pouch 1 and cover the rear 2 and front 3 walls respectively. The rear comfort layer 5 also comprises a wafer aperture that is in register with the stomal inlet 20 of the rear wall 2, in which the wafer 7 is arranged.

The rear comfort layer 5 and the front comfort layer 6 are formed of a flexible sheet material comprised of a woven fabric layer which is laminated across its entire surface to a continuous layer of film material. The continuous layer of film material forms an uninterrupted, solid layer having no voids, thus completely covering one surface of the comfort layer 6, namely its inside surface in use.

In this embodiment, the fabric layer forms the outside surface of the rear 5 and front 6 comfort layers respectively, with the continuous layer of film material disposed on the corresponding inside surfaces, facing the rear 2 and front 3 walls. Other embodiments may comprise additional fabric layers and/or film layers as required. In this embodiment, the woven fabric layer comprises polyester but in other embodiments any one or more of nylon, viscose, polyethylene and polypropylene could be used in addition or as an alternative.

In this embodiment, the woven fabric layer has an area density of 58 $g/m^2$, a tensile strength of 280 to 300 N, and a tear strength of 18 N. Other embodiments may have different compositions, for example an area density of 50 to 70 $g/m^2$, a tensile strength of 200 to 400 N, and a tear strength of 10 to 30 N. Some embodiments may also have a colour fastness to any one or more of rubbing, perspiration or washing (40°) of 4 to 5, and an abrasion of >50,000. Certain embodiments also comprise a woven polyester with a water repellent finish. The water repellent finish may be fluorocarbon based and may be dyed heat set or boil off heat set. A suitable woven polyester layer is available from Newton Textiles Limited of Northamptonshire, UK, under the 75DCWR Designation, such as 75DCWRWHITE (for a white variant).

In this embodiment, continuous layer of film material comprises ethylene-vinyl acetate (EVA).

In this embodiment, the continuous layer of film material has an area density of 23 $g/m^2$. A suitable EVA film is available from Protechnic SA of Cernay, France under the designation 3X9S23.

The continuous layer of film material is laminated to the fabric layer over the entire area of the inside surface of the rear 5 and the front 6 comfort layers. Lamination, e.g. calendaring at elevated temperature and pressure, creates a laminate in which the continuous layer of film material extends across the entire area of the comfort layers 5, 6 with an even thickness throughout and no voids therein. Because the EVA film in question is adhesive at elevated temperature, no intervening adhesive layer is between the continuous film and the comfort layer, rather, the continuous layer of film material is laminated directly to the comfort layer.

Advantageously, the provision of the continuous layer of film material allows both comfort layers 5, 6 and both walls 2, 3 to be joined together simultaneously in the same welding process if desired, in the same manner as a non-woven material would be attached, improving the bond, without the need for specialist intervening layers or the application of adhesive during the construction process. In this embodiment, the peripheral weld defined by the edge seal 8 also joins the rear comfort layer 5 to the rear wall 2 and the front comfort layer 6 to the front wall 3. In other embodiments, various welds may be used as required or desired. For example, the weld may only correspond to a portion of the weld joining the rear 2 and front 3 walls. The weld attaching the rear comfort layer 5 to the rear wall 2 may be different from the weld attaching the front comfort layer 6 to the front wall 3. In addition, the continuous layer of film material protects the fabric layers from undesirable fraying.

In this embodiment, the front comfort layer 6 comprises an upper part **6*a* and a lower part 6*b*, which when taken together are the same shape as the front wall 3. The upper 6*a* extends from the top of the pouch 1 to the point of inflection 17 between the upper section 10 and waisted section 12. The lower part 6*b* extends from the bottom of the pouch 1, beneath the upper part 6*a* to a point slightly above the point of inflection 17. As such, the upper 6*a* part partially overlaps the lower part 6*b* in an overlap region 115. The upper part 6*a* and the lower part 6*b* are separable from each other in the overlap region 115 to form a window opening for viewing the cavity. The overlap region 115 extends horizontally when the ostomy pouch 1 is in use. In some embodiments, the overlap region 115 may not coincide with the point of inflection 17 and may span the pouch 1 at any suitable location along its length. Importantly, without the presence of the continuous layer of film material, the two parts 6*a*, 6*b*, of the front comfort layer 6 would not bond to one another at all, regardless of the choice of material for the walls 2,3**, because the material of the wall is not involved in the bond in that region.

In other embodiments, the front layer may be comprised of multiple parts. The external shape and dimensions of the multiple parts when taken together may be the same as that of the front wall 3.

In this embodiment, the ostomy wafer 7 is in register with the stomal inlet 20 of the rear wall 2 and extends through the wafer aperture of the rear comfort layer 5. The ostomy wafer 7 comprises an adhesive and a release liner 31. The ostomy wafer 7 is mounted to the rear wall 2 by welding. In other embodiments the wafer 7 may be mounted by any suitable alternative means (e.g. adhesive).

The ostomy pouch 1 may also be provided with a gas vent for venting of stomal gases from the cavity. In this embodiment, the ostomy pouch 1 comprises a gas vent filter 24 which is also an odour filter. Suitable filters could be a charcoal or activated carbon filter, for reducing the release of unwanted odours from the cavity. The gas vent filter 24 forms a part of the gas vent, which comprises a gas vent aperture 27 located in the front wall 3. In some embodiments, the gas vent filter 24 is covered by a filter cap and the gas vent filter 24 and filter cap are located on the front wall 3 over the gas vent aperture 27. The gas vent aperture 27 permits the passage of gas from the cavity towards an exterior of the ostomy pouch through the gas vent filter 24 and filter cap.

In this embodiment, the gas vent is located, in use, in the upper quarter of the ostomy pouch 1. In particular, the centre of the gas vent aperture 27 is disposed, in use, above the centre of the stomal inlet 20. In other embodiments, the gas vent may be located elsewhere in the upper section 10 of the ostomy pouch 1.

In this embodiment, the separation wall 4 is located between the rear wall 2 and the front wall 3. The separation wall 4 comprises a separation filter 100 for filtering stomal gases and/or stomal liquids from stomal solids contained in the stomal output. The separation filter 100 thus prevents stomal solids from contacting the gas vent and clogging or otherwise impairing the functionality of the gas vent filter 24.

In this embodiment, the separation wall 4 has the same external shape and dimensions as the rear wall 2 and the front wall 3 and divides the cavity of the ostomy pouch 1 into a first and a second chamber 101, 102. The first chamber 101 extends between the separation wall 4 and the rear wall 2, and the second chamber 102 extends between the separation wall 4 and the front wall 3. The first and second chambers 101, 102 have substantially the same volume. In other embodiments, they may have different volumes and/or the second chamber 102 may have a larger volume than the first chamber 101.

In this embodiment, the separation wall 4 is joined to the rear wall 2 and front wall 3 at their peripheral edges by use of welding to create a fluid-tight seal therebetween. In another embodiment, the separation wall 4 is joined to the rear 2 and front 3 walls about the whole of the edge of the upper section 10, and is additionally joined to the front wall 3 by a horizontal weld at the interface between the upper 10 and waisted 12 sections. Therefore, the joining of the separation wall 4 with the rear and front walls 2, 3 according to some embodiments of the invention may be such that the first and second chambers 101, 102 are sealed from one another other than via the separation filter 100.

In this embodiment, the separation wall 4 comprises a flexible sheet material, which may be formed of polyurethane, polyethylene (PE), polyvinylidene chloride (PVDC) and/or ethylene-vinyl acetate (EVA). In some embodiments, the flexible sheet material of the separation wall 4 has a thickness of 50 to 150 micrometres, preferably 75 to 100 micrometres. In this embodiment, the separation wall 4 comprises a hydrophobic and oleophobic coating applied to the flexible sheet material. In other embodiments, the flexible sheet material may be hydrophobic and/or oleophobic.

Figure 5:
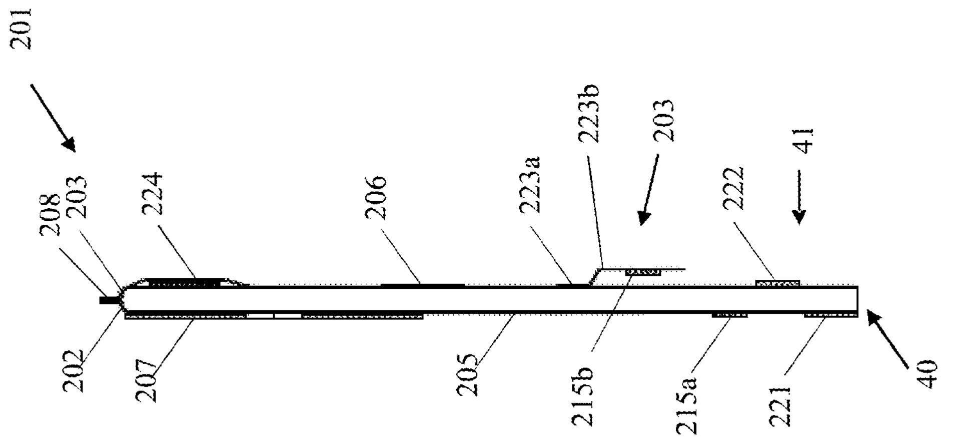
FIG. 5 is a cross-sectional side view of the ostomy pouch of FIG. 4.
Figure 4:
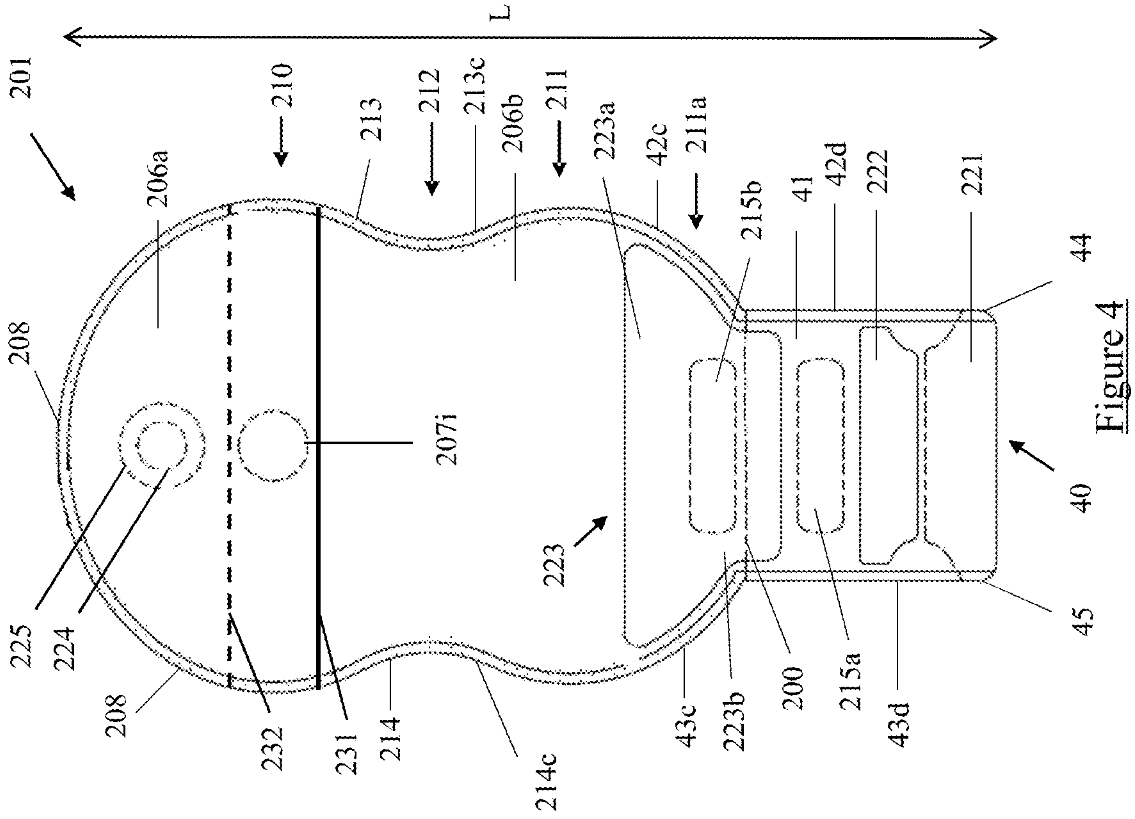
FIG. 4 is a front view of an alternative ostomy pouch.

Referring to FIGS. 4 to 6, a further embodiment of an ostomy pouch 201 according to the present invention is similar to that shown in FIGS. 1 to 3, with like features having similar reference numerals, incremented by 200. The main difference is that the lower section 211 of the further embodiment is shaped to accommodate/form a foldable drain. Thus, in contrast to the embodiments described above, this embodiment of the ostomy pouch 201 is an open pouch that does not comprise a sealed perimeter.

Moreover, in this embodiment, no separation wall is provided between the front 203 and rear 202 walls, and as such the cavity is not divided into two sections. The rear wall 202 features a large opening 202*i* in register with the stomal inlet 207*i* of the wafer 207 (which is connected to the rear wall 202 in the region between the periphery of the opening 202*i* and the periphery of the wafer, such that stomal output enters the cavity via the stomal inlet of the wafer and the opening 202*i* in the rear wall. The rear comfort layer 205 also features an opening 205*i* slightly larger than the opening 202*i* in the rear wall 202 and in register with it, so as to be sandwiched between the outermost edge of the wafer and the rear wall 202. The stomal inlet 207*i* is adjustable to fit the stoma of the ostomate.

In a similar fashion to the first embodiment, the front comfort layer 206 of this embodiment is formed of two parts: an upper part 206*a*; and a lower part 206*b*. The upper part 206*a* overlaps the lower part 206*b* across the majority of the width of the pouch 201 at a point on its height in register with the stomal inlet 207*i*. The overlap being defined by the lower edge 231 of the upper part 206*a* that overlaps the upper edge 232 of the lower part 206*b*.

In this embodiment, there is also an optional gas filter 224 positioned in the front wall 203 at a height above the stomal inlet 207*i* to allow gas to exit the pouch 201. in this embodiment, the filter 224 is covered by an optional filter cover patch 225 (not shown in FIG. 5) on the outside surface of the front wall 203. As such, the filter 224 and filter cover patch 225 are covered by the upper part 206*a* of the front comfort layer 206.

In this embodiment, the lower section 211 comprises a drain aperture 40. The drain aperture 40 is an unsealed portion of the perimeter of the ostomy pouch 201 where the rear 202 and front 203 walls are not scaled.

In this embodiment, the lower section 211 comprises a rounded portion 211*a* and a substantially rectangular drain portion 41 that accommodates the drain aperture 40, with the rounded portion 211*a* being adjacent the waisted section 212 and the drain portion 41 being distal the waisted section 212. The drain portion 41 is foldable along its length between an unfolded and a folded configuration as described later.

In this embodiment, the lower section 211 comprises a continuous left edge 42 that extends from the left edge 213*c* of the waisted section 212 to a left vertex 44 of the drain aperture 40 around the curved left edge 42*c* of the generally rounded portion 211*a* and along a left edge 42*d* of the drain portion 41. Similarly, a continuous right-hand edge 43 extends from the right edge 214*c* of the waisted section 212 to a right vertex 45 of the drain aperture 40 around a continuously curved right edge 43*c* of the generally rounded portion 211*a* and along a right edge 43*d* of the drain portion 41. (Note that as FIG. 4 is a front view, the left edges of the pouch 1 are on the right of the figure and right edges of the pouch 1 on the left of the figure.)

The left 42*d* and right 43*d* edges of the drain portion 41 are parallel to one another along the majority of their length.

In this embodiment, a single continuous edge seal 208 extends around the perimeter of the pouch 201 from the left vertex 44 of the drain aperture 40 to the right vertex 45 of the drain aperture 40, leaving the distal end of the drain aperture 40 open.

In this embodiment, the drain portion 41 defines an elongate drain passage that extends from the cavity of the ostomy pouch 201 to the drain aperture 40 located at a lower end of the drain portion 41. The drain portion 41 is integral with the lower section 211 and as such, the rear wall 202 and the front wall 203 may each be a single piece of material that includes the upper section 210, the waisted section 212 and lower section 211 (including the drain portion 41). However, in this embodiment, the rear comfort layer 205 and front comfort layer 206 do not cover the drain portion 41 of the rear wall 202 and the front wall 203.

In this embodiment, communication between the cavity and the elongate drain passage is via a drain inlet 200 defined as the point of transition between the cavity and the drain portion 41. The drain inlet 200 allows passage of stomal output from the cavity into the drain portion 41 when the drain portion 41 is unfolded.

In this embodiment, movement of the drain portion 41 between its unfolded or folded configuration opens or closes the drain aperture 40. This either permits or prevents outflow of the stomal output stored in the ostomy pouch 1 cavity.

In this embodiment, the drain portion 41 can be repeatedly folded in the same sense along its length into a plurality of segments having approximately equal segment lengths and separated by folds. The drain portion 41 may therefore be successively folded one or more times such that the segments overlie each other. Each fold is formed across the width of the drain portion 41 and acts to inhibit and preferably prevent passage of stomal output out of the drain aperture 40.

In this embodiment, first 221 and second 222 pursing strips are provided on the drain portion 41. The pursing strips 221, 222 provide both localised rigidity to the drain portion 41 and also define the locations and orientations of the segments and folds of the drain portion 41. The pursing strips 221, 222 comprise strips of flexible material attached drain portion 41, wherein the strips 221, 222 have a higher rigidity than the material of the drain portion 41. The pursing strips 221, 222 also have some resilience such that once attached to the drain portion 41, the pursing strips 221, 222 can each be squeezed laterally to arch the pursing strip and thereby open the elongate drain passage. In other embodiments, two or more pursing strips may be used.

In this embodiment, the pursing strips 221, 222 are formed from polystyrene, but other embodiments may comprise any suitable material.

In this embodiment, the first pursing strip 221 is attached to the rear wall 202 of the drain portion 41 adjacent the drain aperture 40. The second pursing strip 222 is attached to the front wall 203 of the drain portion 41 above the second strip 222. A longitudinal gap is provided between an upper edge of the first pursing strip 221 and a lower edge of the second pursing strip 222. The longitudinal gap therefore defines the location of a first fold of the drain portion 41. Each pursing strips 221, 222 spans the width of the drain portion 41 and extends the same distance along a length of the drain portion 41.

In this embodiment, a rear fastening element 215*a* is arranged on the rear wall 202 and a front fastening element 215*b* is arranged on a flap 223 that is mounted to the front comfort layer 206. In this example of a two-part front comfort layer 206, the flap 223 is mounted to the lower part 206*b* of the comfort layer 206. The rear fastening element 215*a* and the front fastening element 215*b* comprise corresponding hook-and-loop type fastener elements. The rear fastening element 215*a* is located on the drain portion 41 above the second pursing strip 222. A longitudinal gap is provided between an upper edge of the second pursing strip 222 and a lower edge of the rear fastening element 215*a*. The longitudinal gap therefore defines the location of a second fold of the drain portion 41.

In this embodiment, the flap 223 comprises a first flange 223*a* and a second flange 223*b* formed of one integral piece. The first flange 223*a* spans substantially all of the width of the lower rounded section 211*a*, but does not extend over the edge seal 208, at a point one third up the length of the rounded section 211*a* from the drain inlet 200. The first flange 223*a* is attached to the comfort material 206 by a single weld that spans substantially its entire width.

The flap 223 may be formed from the same material as the comfort layer, that is to say, a sheet of woven comfort material, with a continuous layer of film material laminated to its inside surface. A such, the weld between the outside surface of the comfort layer 206*b* to the flap 223 is made possible by the continuous layer of film material which forms the inside surface of the sheet of woven comfort material. The second flange 223*b* extends from the lower edge of the first flange 223*a* and is connected to the pouch 1 only by the first flange 223*a*. The second flange 223*b* is contoured so as to conform to the shape of the rounded portion 211*a* but is thinner, tracing the inside edge of the peripheral weld 208. As such, the second flange 223*b* extends downwards from the first flange 223*a* within the perimeter defined by the edge seal 208 of the pouch 201.

In this embodiment, the flap 223 has an outside surface, facing away from the ostomate in use and an opposite inside surface. The front fastening element 215*b* is located on the inside surface of the second flange 223*b* at a position above the rear fastening element 215*a*. A longitudinal gap is provided between an upper edge of the rear fastening element 215*a* and a lower edge of the front fastening element 215*b* and defines the location of a third fold of the drain portion 41. The flap 223 is formed from a flexible sheet material that is more rigid than the flexible sheet material of the rear wall 202, front wall 203 and comfort layers 205, 206. In this embodiment, the flap 223 is formed from a plastic foam which provides a desirable rigidity.

Folding of the drain portion 41 may be carried out as follows. First, the distal end of the drain portion 41 is folded upwards and away from the rear of the ostomy pouch 201 about the first fold line to locate the first pursing strip 221 over the second pursing strip 222. Secondly, the drain portion 41 and the pursing strips 221, 222 are folded again, in the same sense, about the second fold line and then the third fold line such that the folded and stacked first pursing strip 221, second pursing strip 222 and first fastening element 215*a* are located beneath the second flange 223*b* of the flap 223 with the rear fastening element 215*a* being exposed and adjacent the front fastening element 215*b*. Finally, the second flange 223*b* of the flap 223 is pressed onto the folded drain portion to secure together the rear fastening element 215*a* and the front fastening element 215*b*.

In these embodiments, the drain portion 41 can then be unfolded by reversing the above procedure.

As in the first embodiment, in the second embodiment, the rear comfort layer 205 and the front comfort layer 206 are formed of a flexible sheet material comprised of a woven fabric layer with a continuous layer of film material laminated to one surface-its inside surface in use. In this embodiment, the fabric layer is forms the outside surface of the rear 205 and front 206 comfort layers respectively, with the continuous layer of film material disposed on the corresponding inside surfaces, facing the rear 202 and front 203 walls. Other embodiments may comprise additional fabric layers and/or film layers as required. In this embodiment, the woven fabric layer comprises polyester but in other embodiments any one or more of nylon, viscose, polyethylene and polypropylene could be used in addition or as an alternative.

In this embodiment, the woven fabric layer has an area density of 58 g/m$^2$, a tensile strength of 280 to 300 N, and a tear strength of 18 N. Other embodiments may have different compositions, for example an area density of 50 to 70 g/m$^2$, a tensile strength of 200 to 400 N, and a tear strength of 10 to 30 N. Some embodiments may also have a colour fastness to any one or more of rubbing, perspiration or washing (40°) of 4 to 5, and an abrasion of >50,000. Certain embodiments also comprise a woven polyester with a water repellent finish. The water repellent finish may be fluorocarbon based and may be dyed heat set or boil off heat set. A suitable woven polyester layer is available from Newton Textiles Limited of Northamptonshire, UK, under the 75DCWR Designation, such as 75DCWRWHITE (for a white variant).

In this embodiment, the continuous layer of film material has an area density of 23 g/m$^2$. A suitable EVA film is available from Protechnic SA of Cernay, France under the designation 3X9S23.

In this embodiment, the continuous layer of film material is once again laminated directly onto the fabric layer over an entire area of the inside surface of the rear 205 and the front 206 comfort layers, with no intervening adhesive required, because the film layer itself is adhesive at elevated temperatures.

Advantageously, as in the first embodiment the use of the continuous layer of film material allows both comfort layers 205, 206 and both walls 202, 203 to be joined together simultaneously in the same welding process if desired, in the same manner as a non-woven material would be attached, without the need for specialist intervening layers or the application of adhesive during the construction process and with adhesion even in regions where woven layers are joined to each other (i.e. the overlap). In this embodiment, the peripheral weld defined by the edge seal 208 also joins the rear comfort layer 205 to the rear wall 202 and the front comfort layer 206 to the front wall 203. In other embodiments, various welds may be used as required or desired. For example, the weld may only correspond to a portion of the weld joining the rear 202 and front 203 walls. The weld attaching the rear comfort layer 205 to the rear wall 202 may be different from the weld attaching the front comfort layer 206 to the front wall 203.

Referring to FIG. 7, apparatus for use in a method of forming the pouches of the invention is shown schematically. In this embodiment, an apparatus 300 comprises four rollers 301, 302, 303 and 304, a stamp welding machine 305, and a cutting machine 306. The rollers 301, 302, 303, 304 are used to advance a first 311, a second 312, a third 313 and a fourth 314 flexible sheet material respectively in the direction of the arrow, D. For simplicity, additional rollers used to advance the sheet material are not shown.

In this embodiment, the apparatus 300 is configured to construct an ostomy pouch 310 similar to the ostomy pouches 1, 201 of FIGS. 1 to 6 comprising a rear comfort layer 5, 205, rear wall 2, 202, front wall 3, 203 and front comfort layer 6, 206. However, the process is shown simplified, without features such as the separation layer 4 or aspects of the drain portion 41 described in the embodiments above and without any description of the assembly of the wafer, filter and so forth, which can be provided in manner which will be well known to those skilled in the art.

The first 311 and second 312 sheets of material are plastics film used for the rear and front walls of the pouch 310 respectively. As such, the materials used for these sheets are the same and correspond to that described in relation to the ostomy pouches 1, 201 described above.

In this embodiment, the third 313 and fourth 314 sheets of material are used for the rear and front comfort layers of the pouch 310 respectively. As described above, the material used for the comfort layers comprise a woven fabric layer with a continuous layer of film material laminated thereto. As such, the third 313 and fourth 314 sheets of material comprise a woven fabric layers 313*a*, 314*a* each having a continuous layer 313*b*, 314*b* of film material laminated thereto. In FIG. 7, the layers of film material 313*b*, 314*b* face towards one another, with the first and second layers of sheet material 311, 312 which will form the rear and front walls of the cavity arranged between them.

The third 313 and fourth 314 sheets of material have been previously formed in a separate facility, days earlier, by a laminating process, such as a calendaring process, in which a thin, but solid sheet of EVA film 313*b*, 314*b* (having no voids therein) is advanced from a roll and laminated under elevated heat and pressure directly onto sheet of woven material 313*a*, 313*b* similarly advanced from a roll, then cooled and rolled onto a new roll, on which it is delivered. As noted above, no intervening adhesive is provided between the solid sheet of EVA film and the sheet of woven material. This process creates a continuous layer of EVA film with an even thickness across the entire surface of the woven material and avoids the formation of any voids in the continuous layer of EVA film 313*b*, 314*b*. For example, with a laminate of EVA film is available from Protechnic SA of Cernay, France under the designation 3X9S23, on the woven comfort material, the entire surface can be covered by the laminate, and the thickness of the EVA film can be substantially unchanged from its starting thickness of a constant 23.2 μm=/−1 μm across its entire length and width.

In this embodiment, the stamp welding machine 305 is arranged to weld together the layers of material using a hot stamp. The shape of the weld corresponds to the perimeter edge seal 8 as described in the ostomy pouches 1, 201 of FIGS. 1 to 3 and 4-6.

As can be seen from FIG. 8 (a photograph of sheet 313/314 in the region of the perimeter edge seal, 315, 8, 208) the region which has been welded is virtually indistinguishable from the remainder of the sheet of woven material 313, 314. This can be compared visually with the image in FIG. 9, where the welded periphery (P) is clearly distinguishable, because of its mottled edge, with unsightly dark spots (S) (not all of which are labelled).

Referring back to FIG. 7, in this embodiment, the cutting machine 306 is arranged to cut sections of the advancing sheet of material in the shape defined by the perimeter of the ostomy pouch.

In this embodiment, first, the first 311 and second 312 sheets of material are brought together by rollers (not shown) such that they are in contact and advance at the same rate as one another. Next, the third 313 and fourth 314 sheets of comfort material are brought together on opposite sides of the first 311 and second 312 sheets of film material by rollers (not shown). The third sheet 313 is brought adjacent to the first sheet 311 such that the continuous layer of film material 313*b* faces the first sheet 311. Similarly, the fourth sheet 314 is brought adjacent the second sheet 213 such that the continuous layer of film material 314*b* faces the second sheet 312. As such, all four sheets are in contact and advance at the same rate. The sheets thus are stacked in the following order: third 313; first 311; second 312; and, fourth 314.

In this embodiment, the advancing sheet of material then enters the stamp welding machine 305. The stamp welding machine 305 applies the heated stamp to the advancing sheet creating a sealed weld line 315 that corresponds to the perimeter of the ostomy pouch 310. The heated stamp can be applied either to the comfort layer which will be at the rear in use, or that which will be at the front, since direct application of heat does not cause the continuous layer of film material to leak through the fabric layer and cause unsightly mottling/spotting. This is to be contrasted with the approach of PCT/GB2021/051340, where despite rigorous testing of various different webs of EVA, one could not be found that did not leak through the fabric, at least on one side.

The continuous layers of film material 313*b* and 314*b*, facilitate the fabric layers 313*a* and 314*a* welding to the first 311 and second 312 layers—this is especially the case where the continuous layers of film material 313*b*, 314*b* are formed from the same material as the first and second layers 311, 312, e.g. when they are all EVA. This process generates a series of sealed ostomy pouches 310 in the advancing sheets. In this embodiment, the stamping machine only welds around the perimeter of the pouches, leaving a cavity within the pouch 310.

In this embodiment, the advancing sheets then enter the cutting machine 306. The cutting machine cuts around the perimeter of the sealed weld line 315 created by the stamping machine 305. This frees each ostomy pouch 310 from the advancing sheets where they can be collected or further prepared. Welding and cutting could of course take place simultaneously.

In other embodiments, additional layers of material may be introduced. In one embodiment, a fifth sheet of comfort layer material is used (not shown) and is applied on the same side of the pouch as the third 313 sheet. This allows the front comfort layer to be comprised of an upper part 6*a* and lower part 6*b* or 6*bi* as described in relation to FIGS. 1 to 3 above, where for example, the third layer forms the lower part and the fifth layer forms the upper part. Advantageously, the third 313 and fifth sheets can be welded to the pouch simultaneously with the other layers, forming the pouch with an overlapping region 115 in a single stamp welding process.

The one or more embodiments are described above by way of example only. Many variations are possible without departing from the scope of protection afforded by the appended claims.

The invention claimed is:

1. An ostomy pouch comprising a cavity for storing stomal output;

the cavity defined by a rear wall and a front wall joined at their peripheries and formed of flexible sheet material;

the ostomy pouch further comprising a sheet of woven comfort material covering the outside surface of the front wall;

the sheet of comfort material having an outside surface and an opposite inside surface, wherein the outside surface of the sheet of comfort material forms at least part of the outside surface of the pouch, and the inside surface of the sheet of comfort material is laminated across its entire surface to a continuous layer of film material, with no intervening adhesive;

the continuous layer of film material having no voids, and at least part of the continuous layer of film material being adjacent, facing and unbonded to the outside surface of the front wall.

2. An ostomy pouch according to claim 1 wherein the continuous layer of film material has an even thickness across the entire surface of the sheet of woven comfort material.

3. An ostomy pouch according to claim 1 wherein the continuous layer of film material has thickness of less than 40 microns across the entire surface of the sheet of woven comfort material.

4. An ostomy pouch according to claim 1 wherein the continuous layer of film material has an area density of 18-30 $g/m^2$.

5. An ostomy pouch according to claim 1 wherein the continuous layer of film material is formed of the same material as the front wall and the rear wall.

6. An ostomy pouch according to claim 1 wherein the continuous layer of film material and the front and rear walls are formed of polymers with the same chemical structure.

7. An ostomy pouch according to claim 1 wherein the continuous layer of film material and the front and rear walls are formed of polymers with the same molecular weight $M_n$.

8. An ostomy pouch according to claim 1 wherein the continuous layer of film material and the front and rear walls are formed of polymers obtained from the same source, with the same designation.

9. An ostomy pouch according to claim 1 wherein the continuous layer of film material is formed of EVA.

10. An ostomy pouch according to claim 9 wherein the front and rear walls are formed of EVA.

11. An ostomy pouch according to claim 1 wherein the continuous layer of film material has an area density of at least 5 $g/m^2$, and no more than 50 $g/m^2$.

* * * * *